US008481273B2

(12) United States Patent
Farach-Carson

(10) Patent No.: US 8,481,273 B2
(45) Date of Patent: Jul. 9, 2013

(54) PERLECAN FRAGMENTS AS BIOMARKERS OF BONE STROMAL LYSIS

(75) Inventor: Mary C. Farach-Carson, Houston, TX (US)

(73) Assignee: University of Delaware, Newark, DE (US)

( * ) Notice: Subject to any disclaimer, the term of this patent is extended or adjusted under 35 U.S.C. 154(b) by 742 days.

(21) Appl. No.: 12/485,640

(22) Filed: Jun. 16, 2009

(65) Prior Publication Data

US 2010/0021934 A1 Jan. 28, 2010

Related U.S. Application Data

(60) Provisional application No. 61/074,424, filed on Jun. 20, 2008.

(51) Int. Cl.
*G01N 33/53* (2006.01)
(52) U.S. Cl.
CPC ............. *G01N 33/53* (2013.01); *Y10S 436/811* (2013.01)
USPC ............ 435/7.1; 435/7.92; 436/501; 436/811
(58) Field of Classification Search
None
See application file for complete search history.

(56) References Cited

U.S. PATENT DOCUMENTS

| | | | |
|---|---|---|---|
| 5,482,856 A | 1/1996 | Fell, Jr. et al. | |
| 6,432,636 B1 | 8/2002 | Maresh et al. | |
| 6,645,770 B2 | 11/2003 | Pollak et al. | |
| 6,821,947 B2 | 11/2004 | Iozzo | |
| 6,855,801 B1 | 2/2005 | San Antonio et al. | |
| 7,094,580 B2 | 8/2006 | Castillo et al. | |
| 7,189,507 B2 | 3/2007 | Mack et al. | |
| 7,191,068 B2 | 3/2007 | Rosenfeld et al. | |
| 2003/0027768 A1 | 2/2003 | Mazar et al. | |
| 2003/0153734 A1* | 8/2003 | Castillo et al. ................ | 530/370 |
| 2004/0115629 A1 | 6/2004 | Panzer et al. | |
| 2005/0170351 A1 | 8/2005 | Tan et al. | |
| 2006/0008803 A1 | 1/2006 | Brunner et al. | |

OTHER PUBLICATIONS

Oda et al., Purification and characterization of perlecan fragment in urine of end-stage renal failure patients, Clinica Chimica Acta 255, 1996, pp. 119-132.*
Balasubramani et al., Perlecan and its immunoglobulin like domain IV are abundant in vitreous and serum of the chick embryo, Matrix Biology 23, 2004, pp. 143-152.*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
Eva M. Gonzalez, et al., "BMP-1/Tolloid-like Metalloproteases Process Endorepellin, the Angiostatic C-terminal Fragment of Perlecan," *The Journal of Biological Chemistry*, vol. 280, 2005, pp. 7080-7087.
Pierluigi Mauri, et al., "Identification of Proteins Released by Pancreatic Cancer Cells by Multidimensional Protein Identification Technology: A Strategy for Identification of Novel Cancer Markers," *The FASEB Journal*, 2005, pp. 1-22.
Mary C. Farach-Carson et al., "Heparan Sulfate Proteoglycans: Key Players in Cartilage Biology," *Critical Review™ in Eukaryotic Gene Expression*, vol. 15, 1, No. 1 2005, pp. 29-48.
Douglas M. Noonan, et al., "The Complete Sequence of Perlecan, a Basement Membrane Heparan Sulfate Proteoglycan, Reveals Extensive Similarity with Laminin A Chain, Low Density Lipoprotein-Receptor, and Neural Cell Adhesion Molecule," *The Journal of Biological Chemistry*, vol. 266, No. 34, 1991, pp. 22939-22947.
Karen Schofield, et al., "Expression of Proteoglycan Core Proteins in Human Bone Marrow Stroma," *Biochem. J.*, vol. 343, 1999, pp. 663-668.
Hans-Georg Koop, et al., "The Bone Marrow Vascular Niche: Home of HSC Differentiation and Mobilization," *Physiology*, vol. 20, 2005, pp. 349-356.
Gregory Bix et al., "Endorepellin causes endothelial cell disassembly of actin cytoskeleton and focal adhesions through α2β1 integrin," *The Journal of Cell Biology*, vol. 166, No. 1, pp. 97-109, 2004.
John M. Whitelock, et al., "The Degradation of Human Endothelial Cell-derived Perlecan and Release of Bound Basic Fibrolast Growth Factor by Stromelysin, Collagenase, Plasmin, and Heparanases," *The Journal of Biological Chemistry*, vol. 271, No. 17, 1996 pp. 10079-10086.
Mary C. Farach-Carson et al., "Perlecan: A Multifunctional Extracellular Proteoglycan Scaffold," *The Author 2007*, Oxford University Press, pp. 1-29.
K. Fjeldstad et al., "Decreasing the Metastatic Potential in Cancers—Targeting the Heparan Sulfate Proteoglycans," *Current Drug Targets*, vol. 6, 2005, pp. 665-682.
Conor C. Lynch, et al., "Matrix metalloproteinases in tumor—host cell communication," *Differentiation*, vol. 70, 2002, pp. 561-573.
Yun-Ge Zhao et al., "Activation of Pro-gelatinase B by Endometase/Matrilysin-2 Promotes Invasion of Human Prostate Cancer Cells," *The Journal of Biological Chemistry*, vol. 278, No. 17, 2003, pp. 15056-15064.
Milton W. Datta et al., "Perlecan, a candidate gene for the CAPB locus, regulates prostate cancer cell growth via the Sonic Hedgehog pathway," *Molecular Cancer*, vol. 5, No. 9, pp. 1-15.
Zhongjun Zhou et al., "Impaired Angiogenesis, Delayed Wound Healing and Retarded Tumor Growth in Perlecan Heparan Sulfate-Deficient Mice," *Cancer Research*, vol. 64, 2004, pp. 4699-4702.
Lucienne Chatenoud, "Monoclonal Antibody-Based Strategies in Autoimmunity and Transplantation," *Method Mol. Med.*, vol. 109, 2005, pp. 297-328.
G. Köhler et al., "Continuous cultures of fused cells secreting antibody of predefined specificity," *Nature*, vol. 256, 1975, pp. 495-497.
Peter T. Jones et al., "Replacing the complementarity-determining regions in a human antibody with those from a mouse," *Nature*, vol. 321, 1986, pp. 522-525.
Philip R. Tempest et al., "Reshaping a Human Monoclonial Antibody to Inhibit Human Respiratory Syncytial Virus Infection In Vivo," *Biotechnology*, vol. 9, 1991, pp. 266-273.

(Continued)

*Primary Examiner* — Gary W Counts
(74) *Attorney, Agent, or Firm* — RatnerPrestia

(57) ABSTRACT

A method for the detection in a body fluid of perlecan polypeptide fragments that are biomarkers of tumor metastasis, and antibodies for detecting these fragments are described. An immunoassay kit for detecting the presence of these biomarkers in a body fluid, such as serum or urine, is also described.

3 Claims, 4 Drawing Sheets

OTHER PUBLICATIONS

Shunji Matsunaga et al., "Temporal and spatial expressions of transforming growth factor-βs and their receptors in epiphyseal growth plate," *International Journal of Oncology*, vol. 14, 1999, pp. 1063-1067.

J. J. Kerrigan, et al., "Matrix Turnover," *Journal of Orthodontics*, vol. 27, No. 3, 2000, pp. 227-233.

Wei Li, et al., "Basement Membrane Dissolution and Reassembly by Limbal Corneal Epithelial Cells Expanded on Amniotic Membrane," *Investigative Ophthalmology & Visual Science*, 2006, vol. 47, No. 6, pp. 2381-2389.

* cited by examiner

SEQUENCE LISTING

```
<160> NUMBER OF SEQ ID NOS: 5

<210> SEQ ID NO 1
<211> LENGTH: 22
<212> TYPE: PRT
<213> ORGANISM: Homo sapiens

<400> SEQUENCE: 1

Glu Cys Val Ala Leu Glu Tyr Arg Cys Asp Arg Arg Pro Asp Cys Arg
1               5                   10                  15

Asp Met Ser Asp Glu Leu
            20

<210> SEQ ID NO 2
<211> LENGTH: 16
<212> TYPE: PRT
<213> ORGANISM: Homo sapiens

<400> SEQUENCE: 2

Gly His Cys Ile Pro Arg Asp Tyr Leu Cys Asp Gly Gln Glu Asp Cys
1               5                   10                  15

<210> SEQ ID NO 3
<211> LENGTH: 18
<212> TYPE: PRT
<213> ORGANISM: Homo sapiens

<400> SEQUENCE: 3

Cys Glu Ser Cys Ala Pro Gly Tyr Glu Gly Asn Pro Ile Gln Pro Gly
1               5                   10                  15

Gly Lys

<210> SEQ ID NO 4
<211> LENGTH: 17
<212> TYPE: PRT
<213> ORGANISM: Homo sapiens

<400> SEQUENCE: 4

Thr Trp Ser Lys Val Gly Gly His Leu Arg Pro Gly Ile Val Gln Ser
1               5                   10                  15

Gly

<210> SEQ ID NO 5
<211> LENGTH: 16
<212> TYPE: PRT
<213> ORGANISM: Homo sapiens

<400> SEQUENCE: 5

Leu Leu Phe Ser Gly Gly Lys Ser Gly Pro Val Glu Asp Phe Val Ser
1               5                   10                  15
```

PERLECAN FRAGMENTS AS BIOMARKERS OF BONE STROMAL LYSIS

CROSS-REFERENCE TO RELATED APPLICATIONS

This application claims the benefit of U.S. Provisional Application Ser. No. 61/074,424, filed Jun. 20, 2008.

GOVERNMENT SUPPORT

This invention was made with Government support under the following grant award: NIH/NCI, PO1 CA098912 from the National Institutes of Health. The Government has certain rights in this invention.

BACKGROUND OF THE INVENTION

The perlecan rich extracellular matrix (ECM) in bone marrow generally does not turn over rapidly except in the presence of inflammation or invasive cells. Invading metastatic cells can produce inflammation and so possess both of these features. Metastatic cell invasion of tissue releases enzymes that degrade extracellular matrix and allow expansion of tumor mass into surrounding tissue. Metastatic cancer cells produce heparanase, sulfatases, metalloproteinases (MMPs) such as 72- and 92-kD type IV collagenases (MMP-2, MMP-9 activated by bone), uPA, kallikrein 14, PSA, other MMPs such as stromelysins and matrilysins (MMP-3,7,10), and other collagenases such as MMP-1. BMP1/TLL are secreted MMPs, produced by alternative splicing of the TLL1 gene, that cleave fibrillar and non-fibrillar collagens, certain growth factors, $\alpha_2$-macroglobulin, lysyl oxidases, laminin, and several proteoglycans including perlecan. Gonzalez, et al., *J. Biol. Chem.* 280: 7080-7087, 2005.

Reactive oxygen species (ROS) increase production of and activate MMPs which degrade perlecan into smaller fragments with a wide range of potential bioactivities, and levels of ROS are higher in the vicinity of tumor tissue. Recently, Mauri, et al. have described proteins released by cancer cells that are involved in ECM remodeling, including HSPG2/perlecan, syndecan 4, and β2M. Mauri, et al., *Faseb J.* 19: 1125-1127, 2005.

Perlecan is a large, multifunctional, five domain heparan sulfate proteoglycan found in nearly all basal laminae as well as in the interstitial matrix of certain tissues, including bone marrow stroma. Farach-Carson et al., *Crit. Rev. Eukaryot. Gene Expr.* 15: 29-48, 2005; Noonan, et al., *J. Biol. Chem.* 266: 22939-22947, 1991. Perlecan is expressed constitutively at high levels in bone marrow and is the most abundant heparan sulfate proteoglycan (HSPG) in bone marrow extracellular matrix (Schofield, et al., *Biochem J.* 343: 663-668, 1999). As metastatic cancer cells invade, grow and reproduce in bone marrow, they release enzymes that degrade perlecan. This proteolytic degradation yields small perlecan fragments, which have ready access to the circulatory system from the bone marrow (Kopp, et al., *Physiology* 20: 349-356, 2005). In addition, degradation of perlecan generates bioactive fragments, such as endorepellin, with unique activities distinct from intact perlecan, including modulation of angiogenesis. Bix et al., *J. Cell Biol.* 166: 97-109, 2004.

The exact identities of most perlecan derived fragments have never been reported. Whitelock, et al., reported the degradation of perlecan by several proteases and glycosidases but did not identify the fragments. Whitelock, et al., *J. Biol. Chem.* 271: 10079-10086, 1996. Farach-Carson and Carson have described enzymes that may degrade perlecan, based on known enzyme target sequences in the perlecan protein. Glycobiology 9:897-905, 2007. These are shown in FIG. 1. The large number of proteolytic sites near the C-terminus of perlecan are actively cleaved by the same proteases that are produced by invading cancer cells at sites of tissue invasion, and perlecan expression increases in cancer tissues and cancer cell lines. Fjeldstad and Kolset, *Current Drug Targets* 6: 665-682, 2005; Lynch and Matrisian, *Differentation* 70: 561-573, 2002; Zhao, et al., *J. Biol. Chem.* 278: 15056-15064, 2003; Datta, et al., *Molecular Cancer* 5: 9-23, 2006. However, the sequences of most proteolytic sites in matrix proteins remain unknown, as are the exact identities of proteolytic fragments of perlecan. Additionally, because sequential cleavage by multiple proteases can occur, many novel perlecan-derived fragments can be created and enter the circulatory system.

SUMMARY OF THE INVENTION

In one embodiment, the invention provides an assay to detect biomarkers of tumor cell metastasis in a body fluid comprising the steps of 1) obtaining a sample of body fluid from a subject, 2) exposing the sample to an antibody that specifically binds to an antigen comprising an epitope of perlecan, 3) allowing the formation of antibody-antigen complexes, and 4) detecting the antibody-antigen complexes. The method may include further determining the amount of antibody-antigen complexes in the sample relative to a standard. Also provided are isolated perlecan polypeptide fragments and antibodies immunospecific for these perlecan polypeptide fragments. In a further embodiment, the invention provides an immunoassay kit for detecting perlecan polypeptide fragments in a body fluid. Patient treatment and counseling options are then selected or devised based on use of these methods, antibodies, kits or assays and the resultant detection of the presence or absence of the tumor biomarkers.

DETAILED DESCRIPTION OF THE INVENTION

Figure 1:
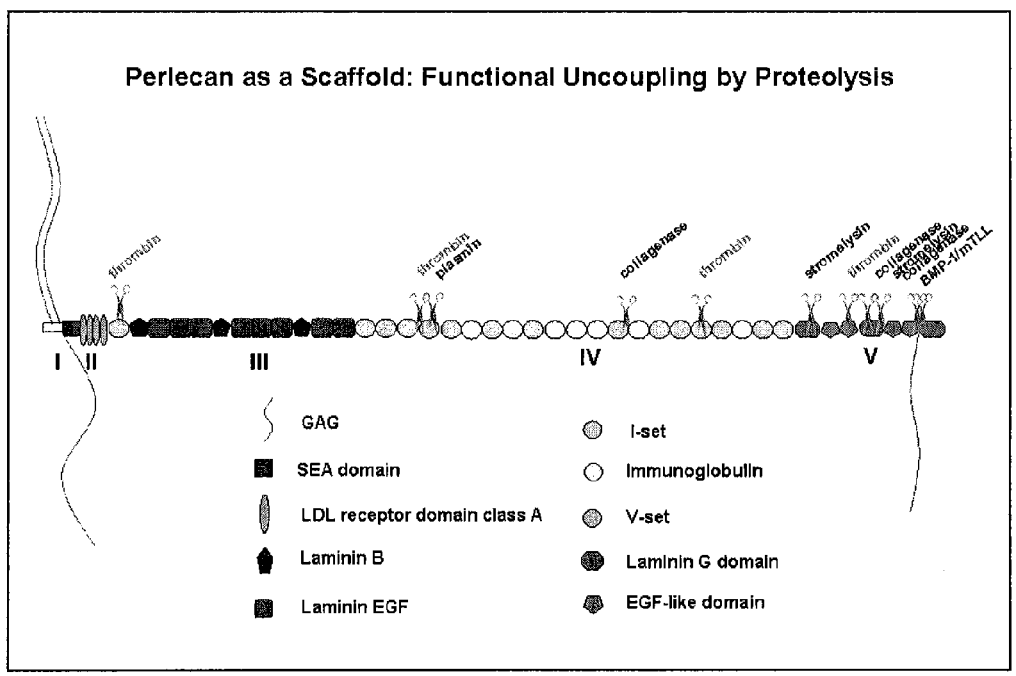
FIG. 1. Diagram of the five domains of perlecan and predicted proteolytic sites in perlecan.
Figure 2:
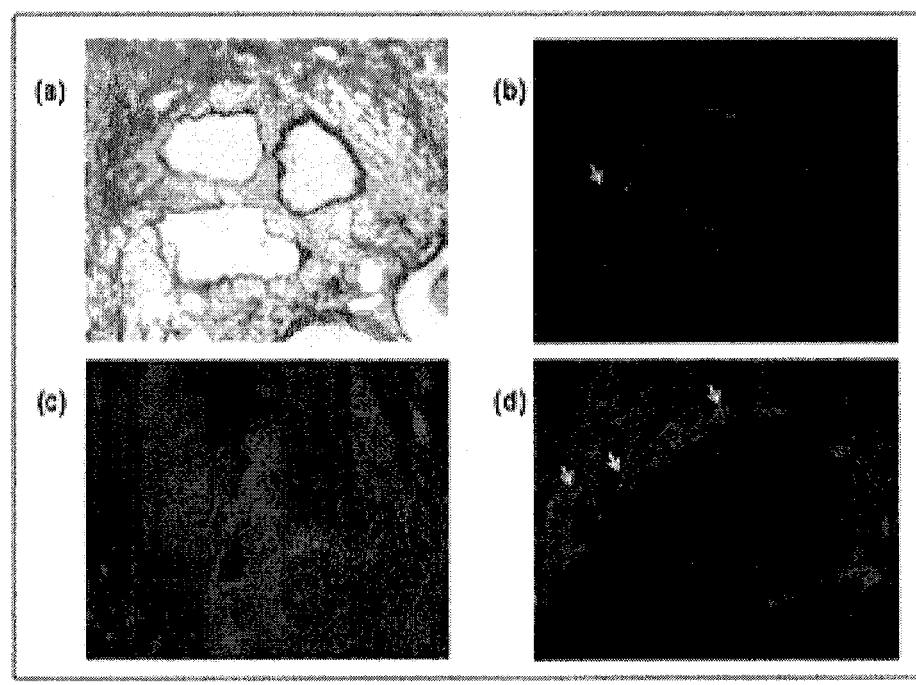
FIG. 2. Expression and localization of perlecan in human tissue of normal and tumorigenic prostate with local invasion.

The studies described in the Examples below demonstrate that the presence of perlecan-derived proteolytic polypeptide fragments in blood samples is correlated with the progression of tumor cell growth and metastasis. "Metastatic" designates a tumor that is invading stroma either locally (as shown in FIG. 2), regionally (as in a lymph node), or distantly (as in bone). These perlecan fragments do not generally enter the circulatory system from tissue that is not being invaded by tumor cells. Accordingly, perlecan fragments can serve as biomarkers for tumor invasion and metastasis. Assays for detection of perlecan fragments in the circulation and in other body fluids provide a method to detect the presence of invasive metastases, including those present in bone marrow that are too small for detection with currently available imaging methods. Unlike other putative cancer biomarkers, the perlecan fragments are derived from normal tissue that is being invaded by metastatic cancer cells, that is, "reactive" tissue, and not from tumor tissue. Therefore, these biomarkers are capable of specifically detecting the presence of metastasis in bone, regardless of cancer origin.

Colonization of bone or stromal tissue by cancer cells introduces malignant cells that are both invasive and inflammatory. Because both basement membrane and bone marrow matrix are rich in perlecan, the presence of growing cancer cells in these environments releases enzymes that create proteolytic fragments of perlecan that circulate as biomarkers of metastatic cancer. Cleavage of perlecan also stimulates neoangiogenesis, increasing the likelihood that the perlecan fragments will enter the bloodstream. Zhou, et al., *Cancer Res.* 64: 4699-4702, 2004. For example, FIG. 2d shows new blood vessels in the vicinity of the tumor (arrows). Perlecan fragments can also enter the urine either via the circulation or, in some cases, from direct invasion of the genitourinary tract by cancer cells.

One embodiment of the invention is an immunoassay method for detecting perlecan fragments in a sample of body fluid, such as blood plasma, serum, or urine. A sample of the body fluid is obtained and reacted with one or more primary antibodies that specifically bind to an antigen comprising an epitope of perlecan. Complexes of antibody-antigen are allowed to form and the sample is then washed to remove unbound antibody or fragments. Antibody-antigen complexes are then detected by any appropriate method. These may include binding the complex with a second antibody or other molecule that is conjugated to a detectable label or adding a detectable label directly to the primary antibody. The amount of label detected can be quantified relative to a standard curve of known amounts of purified perlecan or perlecan polypeptide fragments. Patient treatment and counseling options can then be selected or devised based on the detection and relative amount of the perlecan biomarkers present.

Isolated perlecan polypeptide fragments of the invention include, but are not limited to, those created by digestion with proteases including 72- and 92-kD type IV collagenases, stromelysins, other collagenases, thrombin, and plasmin, as well as recombinant and chemically synthesized perlecan polypeptides. In one embodiment the perlecan polypeptide fragments are derived from perlecan Domains II-V and have the amino acid sequences of SEQ ID NOs: 1-5, described in Example 6.

Antibodies of the invention include any antibody or antibody fragment that is immunospecific for a perlecan fragment found in a body fluid. In one embodiment, the antibody is specific for a perlecan fragment epitope that is not glycosylated. "Immunospecific" means that the antibodies have substantially greater affinity for a specific perlecan epitope than for other polypeptides. Such antibodies may be monoclonal, polyclonal, human, humanized, or chimeric antibodies. Antibody fragments include Fab, Fab', F(ab')2, Fd, Fabc, and Fv molecules. Polyclonal antibodies may be prepared by immunizing an animal with a perlecan polypeptide, and isolating and screening antibodies from the serum of the immunized animal. These methods are well-known in the art. Methods for making and using these and other types of antibodies are also known in the art, for example, as described in Chatenoud, *Methods Mol. Med.* 109: 297-328, 2005; "Production of Monoclonal Antibodies" and "Fragmentation of Immunoglobulins," in *Current Protocols in Immunology*, John Wiley & Sons, 1992; *Monoclonal antibodies: principles and practice*, Academic Press, 1983; Kohler and Milstein, *Nature* 256: 495-497, 1975; *Monoclonal Antibodies and Cancer Therapy*, Alan R. Liss, Inc., 1985; Jones, et al., *Nature* 321: 522-525, 1986; Tempest et al., *Biotechnology* 9: 266-273, 1991; and U.S. Pat. No. 5,482,856.

Figure 3:
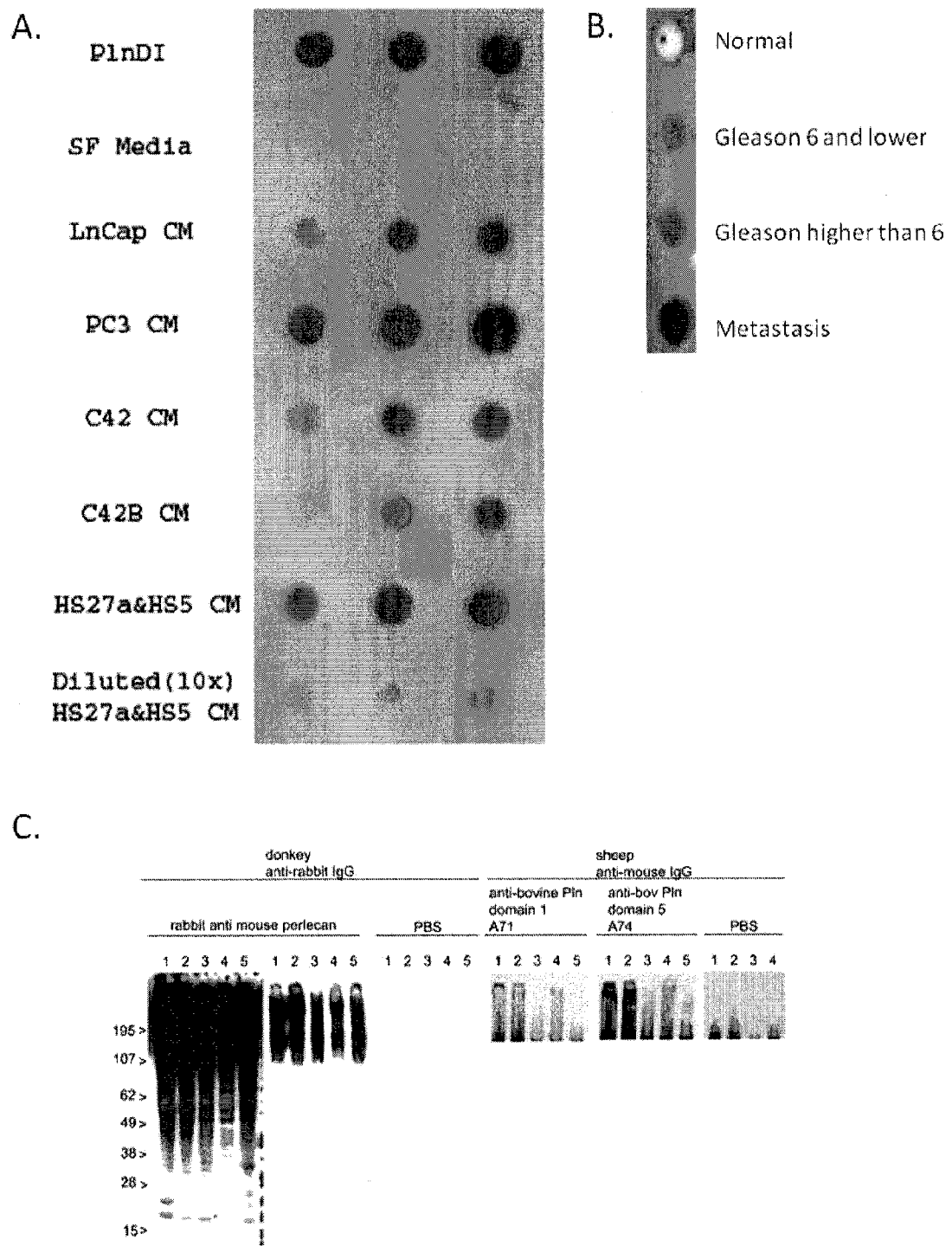
FIG. 3. A. Production of perlecan fragments by prostate cancer cell lines and bone stromal cell lines.
 B. Correlation of relative amount of perlecan fragments in human serum with different stages of prostate cancer.
 C. Perlecan fragments from homogenates of reactive uterine stromal tissue undergoing tissue remodeling.

As shown in FIG. 3B, the relative amount of perlecan polypeptides detected in serum correlates with disease progression in the subject, and is greatest in serum from patients with metastatic tumors. Metastasis from many tumor types and in many tissue types, including, but not limited to, prostate, breast, myeloma, bone, lung, pancreas, colon, liver, kidney, gastrointestinal tract, thyroid, uterus and ovary can be detected in samples of body fluid with this method.

The invention also encompasses an immunoassay kit to be used for detecting perlecan fragments in samples of body fluid. The kit comprises one or more antibodies that detect one or more epitopes of perlecan on a perlecan fragment, and a detectable label. In one embodiment, the antibodies bind to epitopes that are not glycosylated. The detectable label can be directly conjugated to the antibody. Alternatively the detectable label can be used to label the antibody indirectly, such as by conjugation to a secondary antibody, or via biotin-avidin linkage. Detectable labels for use in immunoassays and methods for detecting the labels are known in the art. Suitable detectable labels include, but are not limited to an enzyme label, a radiolabel, a fluorescent label, a chemiluminescent label, a bioluminescent label, or a particulate label. Examples of enzyme labels include horseradish peroxidase, β-galactosidase, and alkaline phosphatase. Examples of radiolabels include $^{32}P$, $^{3}H$, $^{14}C$, $^{35}S$, $^{125}I$, or $^{131}I$. Particulate labels may include latex labels and colloidal metal labels such as colloidal gold, silver, tin, and other metals.

The kit may optionally include a support on which the antibody is bound, a washing solution, and a vessel for reacting the sample with the antibody. Supports include, but are not limited to, glass, plastic, and polymeric substrata.

EXAMPLES

1. Commercially Available Antibodies

Mouse monoclonal antibodies (mAb) that specifically bind to fragments of perlecan domain I (mAbs A71 and A76) and perlecan domain V (mAb A74) were purchased from the Commonwealth Scientific and Industrial Research Organisation (CSIRO), Australia.

2. Expression of Perlecan in Tumor Microenvironment

Normal human prostate tissue and tissue containing prostate tumor tissue from clinical samples were sectioned and stained with H & E (FIG. 2a and c) or reacted with mAB A76 (FIG. 2b and d) using standard methods of histology and immunocytochemistry to assess perlecan expression and distribution.

As shown in FIG. 2b, in normal glandular prostate tissue, perlecan (green) is expressed prominently in basement membranes and in the matrix surrounding the vasculature, but is not seen in the stromal compartment. However, in the prostate tissue surrounding a growing tumor, perlecan expression is prominent in the stroma as well as the local vasculature and new blood vessels (arrows), as seen in FIG. 2d. These results indicate that invasive tumor cells stimulate production and subsequent proteolysis of perlecan by enzymes from the tumor microenvironment, leading to the presence of perlecan polypeptide fragments in the tissue surrounding the growing tumor.

3. Presence of Perlecan Fragments in Culture Medium of Normal and Prostate Cancer Cells Conditioned medium (serum-free DMEM) was collected after one week from cultures of LnCap, PC3, C42, and C42B prostate tumor cell lines and from HS27 and HS5 bone marrow stromal cell lines. The medium was concentrated via DEAE-sepharose. A volume of concentrated medium corresponding to medium from 200,000 cells was dot-blotted onto a nitrocellulose membrane in a total volume of 100-200 µl using standard techniques. After blotting, the membrane was blocked in phosphate buffered saline, pH 7.4, containing Tween 20® (Polyoxyethylene (20) sorbitan monolaurate, ICI Americas, Inc.) (0.05%) (PBS-T) and 3% bovine serum albumin (BSA) overnight at 4° C. After blocking, the membrane was reacted with mAB A76 at a 1:5000 dilution overnight. The membrane was then washed with PBS-T and subsequently reacted with an HRP-conjugated sheep anti-mouse secondary antibody at a dilution of 1:200,000 for 40 minutes. After washing, antibody binding was detected using Pierce #34075 SuperSignal chemiluminescent substrate according to manufacturer's instructions.

Figure 4:
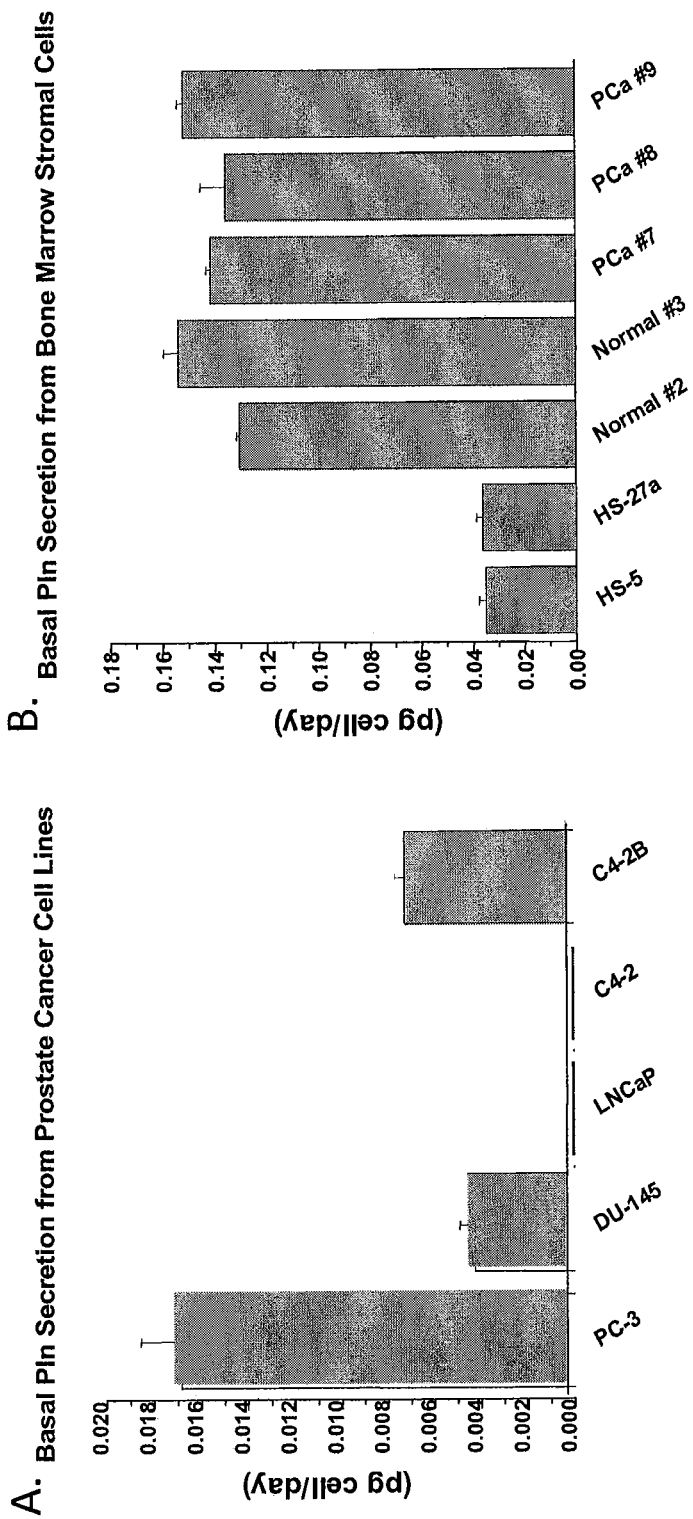
FIG. 4. A. Basal perlecan secretion form prostate cancer cell lines.
 B. Basal perlecan secretion from bone marrow stromal cells. HS-5 and HS-27a are cell lines of normal bone marrow stromal cells. Other samples are culture medium from primary cultures of bone marrow biopsies from normal donors and prostate cancer (PCa) patients.

FIG. 3A shows the resulting blot. The positive control is purified perlecan Domain I polypeptide (PlnDI) and the negative control is serum-free medium (DMEM). The results demonstrate that perlecan polypeptides are released into the medium at high levels by prostate cancer cells and at even higher levels by bone marrow stromal cells. Similar results are shown graphically in FIG. 4.

4. Perlecan Fragments in Uterine Tissue Homogenates

Reactive uterine stroma (but not tumor tissue) was homogenized in RIPA buffer and prepared for gel electrophoresis. Samples containing equal amounts of protein were separated by SDS-PAGE in MES (2-(N-morpholino)ethanesulfonic acid) buffer. Proteins were then transferred to nitrocellulose membranes and reacted with various perlecan antibodies. FIG. 3C shows that multiple sizes of perlecan polypeptide fragments were detected in each sample, demonstrating that reactive uterine stromal tissue is rich in proteolytic polypeptide fragments of perlecan.

5. Correlation Between Serum Immunoreactivity and Metastasis

Biopsy samples of normal and cancerous human prostate tissue were examined microscopically and assigned a Gleason score. The Gleason Score is a grading system for prostate cancer that is used to identify the development of the cancer tissue and to evaluate the prognosis of men with prostate cancer. Gleason grades range from 1 (tissue resembles normal prostate) to 5 (tissue lacks glands). A composite score is assigned based on the most common and the second most common feature of several sites in the biopsy. Higher Gleason scores are predictive of poorer prognosis. The grading system is further described in www.phoenix5.org/infolink/gleason-grading.

Sera from patients who provided the biopsy samples were reacted with mAb A74. Identical amounts (2 µl) of serum from each patient were blotted onto nitrocellulose membranes and processed as described in Example 3, except that mAb A74 was used as primary antibody at a dilution of 1:10,000. Results are shown in FIG. 3c.

Serum from subjects with normal prostate tissue showed very poor immunoreactivity with the antibody. However, immunoreactivity increased in sera from subjects with prostate cancer as Gleason scores increased and was markedly higher in serum from subjects with metastasis. These results demonstrate a correlation between the progression and metastasis of prostate cancer and the amount of perlecan polypeptides in human serum, and demonstrate that perlecan fragments can serve as serum biomarkers for tumor metastasis.

6. Preparation of Antibodies Immunospecific for Proteolytic Perlecan Fragments Five perlecan polypeptide sequences, shown below, were selected and polypeptides having these sequences were synthesized by SynPep, Dublin, Calif.

```
                                      (SEQ ID NO: 1)
    ECVALEYRCD RRPDCRDMSD EL
    (from Domain II of perlecan)

(SEQ ID NO: 2)
    GHCIPRDYLC DGQEDC
    (from Domain II of perlecan)

(SEQ ID NO: 3)
    CESCAPGYEG NPIQPGGK
    (from Domain III of perlecan)

(SEQ ID NO: 4)
    TWSKVGGHLR PGIVQSG
    (from Domain IV of perlecan,
    also described in U.S. 10/363,376)

(SEQ ID NO: 5)
    LLFSGGKSGP VEDFVS
    (from Domain V of perlecan)
```

These five synthesized perlecan polypeptides were used as immunogens by Bethel Labs, Montgomery, Tex., to raise rabbit polyclonal antibodies. The antibodies were screened to identify antibodies with high immunospecificity for each perlecan polypeptide. Each peptide was coupled to BSA and subjected to gel electrophoresis and immunoblotting. Each selected antibody was immunospecific for its corresponding polypeptide, showed little or no cross-reactivity with other polypeptides, and failed to bind to BSA alone. A combination of the five antibodies recognized perlecan fragments secreted by cultured bone-derived cells.

7. Immunoassay to Detect Perlecan Polypeptides in Samples

The immunospecific antibodies of Example 6 may be used individually or in combination in a standard ELISA assay to detect specific perlecan polypeptides in samples of body fluids. For example, a sample of a body fluid, such as serum or urine, from a subject may be added to wells in a microwell plate to which one or more of the antibodies is bound and allowed to react with the antibody. The wells may then be washed to remove unbound polypeptides and a secondary anti-rabbit antibody conjugated to a detectable label may be added. After allowing reaction, the wells may again be washed and the label may be detected and quantified. Alternatively, the sample may be reacted with the antibody by immunoblotting and antibody detection using standard techniques. Quantification may be based on comparison with a standard curve of known amounts of polypeptide. The amount of antibody bound may be used to determine whether metastatic tumor cells are present.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for detecting tumor cell metastasis in a human subject comprising the steps of:
   (a) exposing a sample of body fluid from the subject to an antibody that is immunospecific for an antigen consisting of an amino acid sequence of SEQ ID NO:1, 2, 3, 4, or 5, wherein the body fluid is selected from the group consisting of blood plasma, serum and urine, whereby an antibody-antigen complex is formed;
   (b) detecting the antibody-antigen complex;
   (c) quantifying the amount of the detected antibody-antigen complex relative to a standard;
   (d) determining the presence of the tumor cell metastasis in the subject based on a higher amount of the detected antibody-antigen complex relative to the standard; and
   (e) selecting or devising treatment or counseling to the subject based on the presence of the tumor cell metastasis in the subject.

2. The method of claim 1, wherein the body fluid is serum or urine.

3. The method of claim 1, wherein the tumor cell metastasis is of a tumor type selected from the group consisting of prostate, breast, myeloma, bone, lung, pancreas, colon, liver, kidney, gastrointestinal tract, thyroid, uterus and ovary.

* * * * *